(12) United States Patent
Ohnishi et al.

(10) Patent No.: US 7,351,419 B2
(45) Date of Patent: Apr. 1, 2008

(54) ORAL PHARMACEUTICAL SUSPENSION OF CEFDINIR CRYSTAL

(75) Inventors: Naozumi Ohnishi, Tokyo (JP); Shuhei Deguchi, Fujiidera (JP); Satoshi Kitamura, Tokyo (JP)

(73) Assignee: Astellas Pharma Inc., Tokyo (JP)

( * ) Notice: Subject to any disclaimer, the term of this patent is extended or adjusted under 35 U.S.C. 154(b) by 0 days.

(21) Appl. No.: 11/289,333

(22) Filed: Nov. 30, 2005

(65) Prior Publication Data

US 2006/0135500 A1 Jun. 22, 2006

Related U.S. Application Data

(60) Provisional application No. 60/631,628, filed on Nov. 30, 2004.

(51) Int. Cl.
*A01N 25/00* (2006.01)
*A61K 31/545* (2006.01)

(52) U.S. Cl. ...................... 424/405; 514/202
(58) Field of Classification Search ................ 424/405
See application file for complete search history.

(56) References Cited

U.S. PATENT DOCUMENTS

| | | | |
|---|---|---|---|
| 4,409,214 A | 10/1983 | Takaya et al. | |
| 4,559,334 A | 12/1985 | Takaya et al. | |
| 4,935,507 A * | 6/1990 | Takaya et al. | 540/222 |
| 6,350,869 B1* | 2/2002 | Sturm et al. | 540/220 |
| 7,022,841 B2 | 4/2006 | Cvetovich et al. | |
| 2003/0204082 A1* | 10/2003 | Manca et al. | 540/222 |
| 2004/0210049 A1 | 10/2004 | Lee et al. | |
| 2004/0242556 A1* | 12/2004 | Dandala et al. | 514/202 |
| 2004/0242557 A1 | 12/2004 | Dandala et al. | |
| 2005/0059818 A1 | 3/2005 | Duerst et al. | |
| 2005/0080070 A1 | 4/2005 | Deshpande et al. | |
| 2005/0080255 A1 | 4/2005 | Kumar et al. | |
| 2005/0119244 A1 | 6/2005 | Monguzzi et al. | |
| 2005/0131079 A1 | 6/2005 | Pujara | |
| 2005/0137182 A1* | 6/2005 | Dandala et al. | 514/202 |
| 2005/0209211 A1* | 9/2005 | Law et al. | 514/202 |
| 2005/0209451 A1 | 9/2005 | Manca et al. | |
| 2005/0215781 A1 | 9/2005 | Chandrasekaran et al. | |
| 2005/0245738 A1* | 11/2005 | Singh et al. | 540/222 |
| 2006/0025399 A1* | 2/2006 | Law et al. | 514/202 |
| 2006/0029674 A1 | 2/2006 | Sever et al. | |
| 2006/0040915 A1 | 2/2006 | Kumar et al. | |
| 2006/0069079 A1 | 3/2006 | Sever et al. | |
| 2006/0074236 A1 | 4/2006 | Pozzi et al. | |
| 2006/0094703 A1 | 5/2006 | Deshpande et al. | |
| 2006/0122165 A1 | 6/2006 | Daemon et al. | |
| 2006/0135500 A1 | 6/2006 | Ohnishi et al. | |
| 2006/0135761 A1 | 6/2006 | Datta et al. | |
| 2006/0142261 A1* | 6/2006 | Law et al. | 514/202 |
| 2006/0142563 A1* | 6/2006 | Law et al. | 540/222 |
| 2006/0167242 A1 | 7/2006 | Berghausen | |
| 2006/0211676 A1* | 9/2006 | Law et al. | 514/200 |

FOREIGN PATENT DOCUMENTS

| | | |
|---|---|---|
| EP | 03 04019 | 2/1989 |
| EP | 1 609 793 A1 | 12/2005 |
| EP | 1609793 A1 * | 12/2005 |
| JP | 62-206199 | 9/1987 |
| WO | 9724358 | 7/1997 |
| WO | 99/055710 | 11/1999 |
| WO | WO 02/098884 | 12/2002 |
| WO | WO 03/050124 A1 | 6/2003 |
| WO | WO 2004/016623 A1 | 2/2004 |
| WO | WO 2004/035800 A2 | 4/2004 |
| WO | WO 2004/046154 A1 | 6/2004 |
| WO | WO 2004/056835 A1 | 7/2004 |
| WO | WO 2004/058695 A1 | 7/2004 |
| WO | WO 2004085443 A1 * | 10/2004 |
| WO | WO 2004/104010 A1 | 12/2004 |
| WO | WO 2004104010 A1 * | 12/2004 |
| WO | WO 2005/030178 A1 | 4/2005 |
| WO | WO 2005/060936 A1 | 7/2005 |
| WO | 2005090360 | 9/2005 |
| WO | WO 2005/090361 A1 | 9/2005 |
| WO | 2006010978 | 2/2006 |
| WO | 2006018807 | 2/2006 |
| WO | 2006035291 | 4/2006 |

OTHER PUBLICATIONS

English Translation of JP 63-35961 to Takaya et al.*
Powers et al, Comparison of the Palatability of the Oral Suspension of Cefdinir vs. Amoxicillin/Clavulanate Potassium, Cefprozil and Azithromycin in Pediatric Patients, 2000, Pediatric Infectious Disease Journal, vol. 19, pp. S174-S180.*
"OMNICEF® (Cefdinir) Capsules OMNICEF® (Cefdinir) For Oral Suspension", URL:http://web.archive.org/web/20010612122933/http://www.rxabbott.com/pdf>, XP-002328280, Sep. 2000, 13 pages.

(Continued)

*Primary Examiner*—Sreeni Padmanabhan
*Assistant Examiner*—Kendra D. Carter
(74) *Attorney, Agent, or Firm*—Oblon, Spivak, McClelland, Maier & Neustadt, P.C.

(57) ABSTRACT

The present invention relates to a novel oral pharmaceutical suspension of Cefdinir crystal. More specifically, the present invention relates to a novel kit for preparation of an oral pharmaceutical suspension containing crystal form C Cefdinir.

24 Claims, 6 Drawing Sheets

OTHER PUBLICATIONS

Mino R. Caira, "Crystalline Polymorphism of Organic Compounds", Topics in Current Chemistry, XP-001156954, vol. 198, 1998, pp. 163-208.

Yoshihiko Okamoto, et al., "Degradation Kinetics and Isomerization of Cefdinir, a New Oral Cephalosporin, in Aqueous Solution. 1", Journal of Pharmaceutical Sciences, vol. 85, No. 9, Sep. 1996, pp. 976-983.

Kazuo Sakane, et al., "Research and Development of New Oral Cephems, Cefixime and Cefdinir"; Fujisawa Pharmaceutical Co., Ltd.; eviews, vol. 113, p. 605-626, 1993, w/ English translation.

Walter Cabri, et al., Cefdinir: A Comparative Study of Anhydrous vs. Monohydrate Form Microstructure and Tabletting Behaviour, European Journal of Pharmaceutics and Biopharmaceutics, vol. 64, No. 2, 2006, p. 212-221.

Akiko Shimizu Ibuka, et al., "Crystal Structure of Extended-Spectrum b-lactamase Toho-1: Insights into the Molecular Mechanism for Catalytic Reaction and Substrate Specificity Expansion," Biochemistry, vol. 42, No. 36, 2003, p. 10634-10643.

Shuhei Deguchi, et al., "Structural Studies on Copper(II) Complex Containing (Z)-2-(2-Aminothiazol-4-yl)-N-(2-hydroxyethyl)-2-(hydroxyimino) acetamide, A Model Compound for A Cephalosporin Antibiotic Cefdinir," Journal of Inorganic Biochemistry, vol. 65, No. 3, 1997, p. 191-197.

Shuhei Deguchi, et al., "Structural Studies on an Iron(III) Complex Containing (Z)-2-(2-aminothiazol-4-yl)-N-(2-hydroxyethyl)-2-(hydroxyimino)acetamide, A Model Compound for a Cephalosporin Antibiotic Cefdinir," Journal of the Chemical Society, Dalton Transactions: Inorganic Chemistry, vol. 9, 1996, p. 1967-1971.

Hisahi Mimura, et al., "Estimation of Grinding Effect on the Solid-State Stability of Cefdinir by Use of Microcalorimetry," Drug Stability, vol. 1, No. 1, 1995, p. 34-39.

Davidovich, et al., Detection of Polymorphism by Powder X-Ray Diffraction: Intergerene by Preferred Orientation, 2004, vol. 7, No. 1, pp. 10, 12, 14, 15 and 100.

Bernstein, Joel, Polymorphism in Molecular Crystals, 2002, Clarendon Press, pp. 117-118 and 272.

Brittain, Harry, G., Polymorphism in Pharmaceutical Solids, 1999, Marcel Dekker, pp. 184-185 and 236.

U.S. Pharmacopia #23, National Formular #18, X-Ray Diffraction, 1995, pp. 1843-1844.

Portyansky, Elena, Bug Beater: Cephalosprin offers Extended Spectrum of Activity, 1996, Drug Topics, vol. 142, No. 2, pp. 28 and 31.

Inamoto, et al., FK 482, A New Orally Active Cephalosporin Synthesis and Biological Properties, 1988, The Journal of Antibiotics, pp. 828-830.

U.S. Food and Drug Administration FDA Approved Label for Omnicef, label approved on Jul. 14, 1999.

* cited by examiner

× 1000

× 5000

Crystal form A

× 1000

× 5000

Monohydrate

ORAL PHARMACEUTICAL SUSPENSION OF CEFDINIR CRYSTAL

REFERENCE TO PRIOR APPLICATION

This application claims priority to U.S. provisional application 60/631,628, filed Nov. 30, 2004, incorporated herein by reference.

TECHNICAL FIELD

The present invention relates to a novel oral pharmaceutical suspension of crystalline Cefdinir. More specifically, the present invention relates to a novel kit for preparation of an oral pharmaceutical suspension containing crystal form C Cefdinir.

BACKGROUND ART

7-[2-(2-aminothiazol-4-yl)-2-hydroxyiminoacetamido]-3-vinyl-3-cephem-4-carboxylic acid (syn isomer), known as Cefdinir, is a cephalosporin antibiotic having high antibiotic activity and broad antibacterial spectrum. Cefdinir was first disclosed in U.S. Pat. No. 4,559,334, which is incorporated herein by reference.

To date, two crystal forms of Cefdinir have been observed and prepared in view of suitability for a pharmaceutical product and ease for handling. One crystal form of Cefdinir (hereinafter referred to as "crystal form A") has been disclosed in, for example, U.S. Pat. No. 4,935,507, incorporated herein by reference, which has been widely used as an oral pharmaceutical suspension form.

Another crystal form of Cefdinir (monohydrate, also referred to as "crystal form B") including its method of preparation has been disclosed in JP Patent application No. 62-206199 found in the file of EP0304019, which is incorporated herein by reference. Recently, crystal form B has also been described in US 2003/0204082 A1. However, crystal form B of Cefdinir has not been used to form oral suspensions.

SUMMARY OF THE INVENTION

In the present application, the present inventors have studied the physicochemical properties of the lower hydrates of Cefdinir, and established the present invention based on the novel knowledge gained from these studies.

Specifically, the present inventors have found that crystal form A of Cefdinir exists in an aggregate of small crystals, whereas the lower hydrates of Cefdinir, such as the monohydrate sometimes called crystal form B, exist in the shape of needles. Furthermore, the present inventors have found that the lower hydrates of Cefdinir transform to another hydrate having 1.5 to two or more waters of hydration per mole of Cefdinir in high moisture condition or aqueous solvent and exist as another crystal form, a higher hydrate. That is, in high moisture condition or aqueous media, the lower hydrates of Cefdinir transform to a higher hydrate (also referred to as "crystal form C") which may be present as the sesquihydrate, dihydrate, trihydrate, trihemyhydrate, tetrahydrate, etc. or mixtures thereof. The term Crystal form C is simply convenient nomenclature for the product which results when one or more Cefdinir lower hydrates are converted into one or more higher hydrates in the presence of moisture or aqueous media. The sedimentation rate of crystal form C in aqueous solvent is lower than that of crystal form A, and dispersibility of crystal form C in aqueous solvent is higher than that of crystal form A. This phenomenon is most likely due to the shape of the lower hydrate crystal and the transformation of the lower hydrate crystal to crystal form C in aqueous solvent. The above-described properties of the lower hydrate and form C found by the present inventors make it easier for people to take an oral pharmaceutical suspension containing Cefdinir and allow for long storage of an oral pharmaceutical suspension containing Cefdinir.

In one aspect, the invention provides a kit for preparation of an oral pharmaceutical suspension of crystal form C Cefdinir, wherein said kit comprises: (a) a composition comprising a lower hydrate of Cefdinir within a first container; and (b) a label or a written material indicating that said composition is admixed with pharmaceutically acceptable aqueous carrier prior to administration, wherein said composition when admixed with said carrier forms an oral pharmaceutical suspension of crystal form C Cefdinir.

In other aspect, the present invention provides an oral pharmaceutical suspension comprising crystal form C Cefdinir and pharmaceutically acceptable aqueous carrier.

In other aspect, the present invention provides a method for preparing an oral pharmaceutical suspension comprising crystal form C Cefdinir, comprising admixing composition containing a lower hydrate of Cefdinir with a pharmaceutically acceptable aqueous carrier.

In other aspect, the present invention provides a crystal form C Cefdinir.

In other aspect, the present invention provides a pharmaceutical composition comprising crystal form C Cefdinir.

DETAILED DESCRIPTION OF THE PRESENT INVENTION

Figure 1:
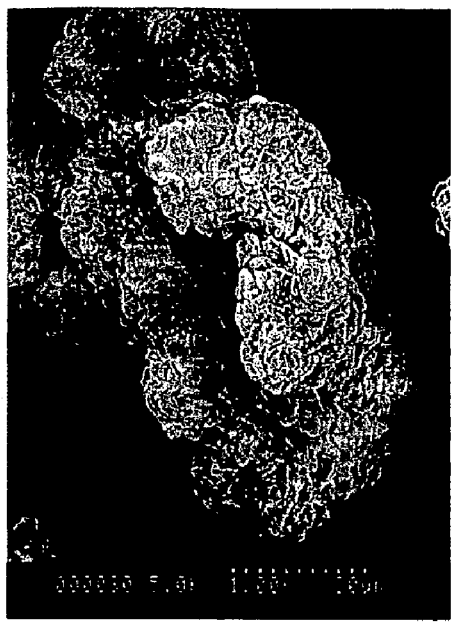
FIG. 1 shows SEM micrographs of crystal form A and the monohydrate of Cefdinir.
Figure 1:
Figure 1:
Figure 1:

The process for preparing Cefdinir is known in the art and has been disclosed in U.S. Pat. No. 4,559,334, incorporated herein.

One process for preparing Cefdinir monohydrate is known in the art and disclosed in JP Patent application No. 62-206199. Another process has been disclosed in US 2003/0204082 A1. The monohydrate obtained may contain some crystal form A.

The term "lower hydrates" includes all hydrated forms of Cefdinir which convert in the presence of water or water moisture into higher hydrates (crystal form C) such as the sesquihydrate and trihemihydrate. One particularly preferred lower hydrate is the monohydrate, sometimes called crystal form B. Lower hydrates may contain up to about 1.25 moles of water per mole of Cefdinir. There is no minimum amount of water which the lower hydrates must contain except that it must be greater than zero. Generally, the lower hydrates will contain from about 0.5 to 1.25 moles of water per mole of Cefdinir, preferably about 1.0. The lower hydrates may contain a mixture of hydrated forms and also may contain some form A, from 0 to 50% by weight.

In one embodiment, the kit of the present invention comprises a composition comprising Cefdinir lower hydrate within a first container and a label or a written material indicating that said composition is admixed with pharmaceutically acceptable aqueous carrier prior to administration, wherein said composition when admixed with said carrier forms an oral pharmaceutical suspension of crystal form C Cefdinir. Preferably, the lower hydrate is the monohydrate. However, so far as oral suspension containing crystal form C Cefdinir can be formed, other crystal form than the lower hydrates of Cefdinir may be used in the composition. Crystal form C in the oral suspension includes any higher hydrate form such as sesquihydrate, dihydrate, trihydrate, trihemyhydrate and tetrahydrate, so far as it is converted from the lower hydrate in the oral suspension. Examples of the oral suspension of the present invention includes, but are not limited to, the oral suspension which mainly contains Cefdinir trihemihydrate containing 3.5 moles of water per mole of Cefdinir. The crystal lattice structure of trihemihydrate contains about 14 moles of water per the unit cell. About 10 moles of water are found in the crystal channels. However, the oral suspension may contain some other higher hydrates of Cefdinir such as sesquihydrate, dihydrate, trihydrate and tetrahydrate.

In one embodiment, the kit further comprises pharmaceutically acceptable aqueous carrier within a second container, wherein said carrier is admixed with said composition to form an oral pharmaceutical suspension of said crystal form C. In another embodiment, the kit further comprises a container used for admixing said composition with said pharmaceutically acceptable aqueous carrier to form an oral pharmaceutical suspension of said crystal form C.

Preferably, said composition comprising Cefdinir lower hydrate is admixed with said pharmaceutically acceptable aqueous carrier to form an oral pharmaceutical suspension of said crystal form C immediately before said oral pharmaceutical suspension is used. Alternatively, multiple doses of said composition comprising Cefdinir lower hydrate may be admixed with said pharmaceutically acceptable aqueous carrier at once and may be preserved for using at a later time.

The oral pharmaceutical suspension of the present invention comprises crystal form C Cefdinir and pharmaceutically acceptable aqueous carrier. The oral pharmaceutical suspension of the present invention can be prepared by admixing Cefdinir lower hydrate with pharmaceutically acceptable aqueous carriers.

The pharmaceutically acceptable aqueous carrier to be used in the present invention includes water and other diluent known in the art suitable for preparing oral pharmaceutical suspension. Preferably, the pharmaceutically acceptable aqueous carrier is water.

The oral pharmaceutical suspension of the present invention may include, if necessary, pharmaceutically acceptable additives including auxiliary substances, stabilizing agents, suspending agents, surface tension modifiers, viscosity modifiers, colorants, preservatives, flavoring agents and other commonly used additives such as lactose, citric acid, tartaric acid, stearic acid, magnesium stearate, sucrose, and the like. In one embodiment, such additive may be included in the composition comprising Cefdinir lower hydrate in the kit of the present invention, and in other embodiment, such additive may be included in the pharmaceutically acceptable aqueous carrier in the kit of the present invention. In one embodiment, the composition comprised in the kit of the present invention contains about 125 mg of a Cefdinir lower hydrate and about 3.0 g sucrose, and the composition can be admixed with 5 ml water as a pharmaceutically acceptable carrier to form an oral pharmaceutical suspension of crystal form C Cefdinir.

The container to be used in the present invention includes, but is not limited, bottle, vial, paper bag, test tube, and pharmaceutically acceptable container known in the art. The container may be formed from one or more materials such as plastic, glass or paper.

The amount of Cefdinir to be contained in the oral pharmaceutical suspension of the present invention may vary and depend upon the age, conditions of the patient, a kind of diseases, etc. In general, amounts between 1 mg and about 4,000 mg or even more per day may be administered to a patient. For example, an average single dose of about 10-1,000 mg, preferably about 50-500 mg, more preferably about 100-250 mg of Cefdinir may be used in treating diseases infected by pathogenic microorganisms.

EXAMPLE

The monohydrate was prepared as follows: Cefdinir (20.0 g) was added to water (200 ml) and the mixture was adjusted to pH 6.0 with saturated sodium bicarbonate aqueous solution. The resultant solution was subjected to a column chromatography on activated charcoal and eluted with 20% aqueous acetone. Fractions were combined and then concentrated to 200 ml. This solution was adjusted to pH 2.2 at 15° C. with 10% hydrochloric acid and stirred at 0° C. for 30 minutes. The resultant crystals were collected by filtration, washed with water and dried to give crystals of Cefdinir monohydrate. The present inventors investigated physicochemical properties for Cefdinir monohydrate and crystal form A. The results are described below.

1. Scanning Electron Microscopy (SEM)

SEM micrographs (HITACHI S-800) of form A and the monohydrate are shown in FIG. 1. It is clear from the figures that form A is an aggregate of small crystals, whereas the monohydrate is a needle shape.

2. Physical Properties

The present inventors investigate the interconversion of the forms as follows.

2-1. Moisture Adsorption/Desorption Isotherm

Figure 2:
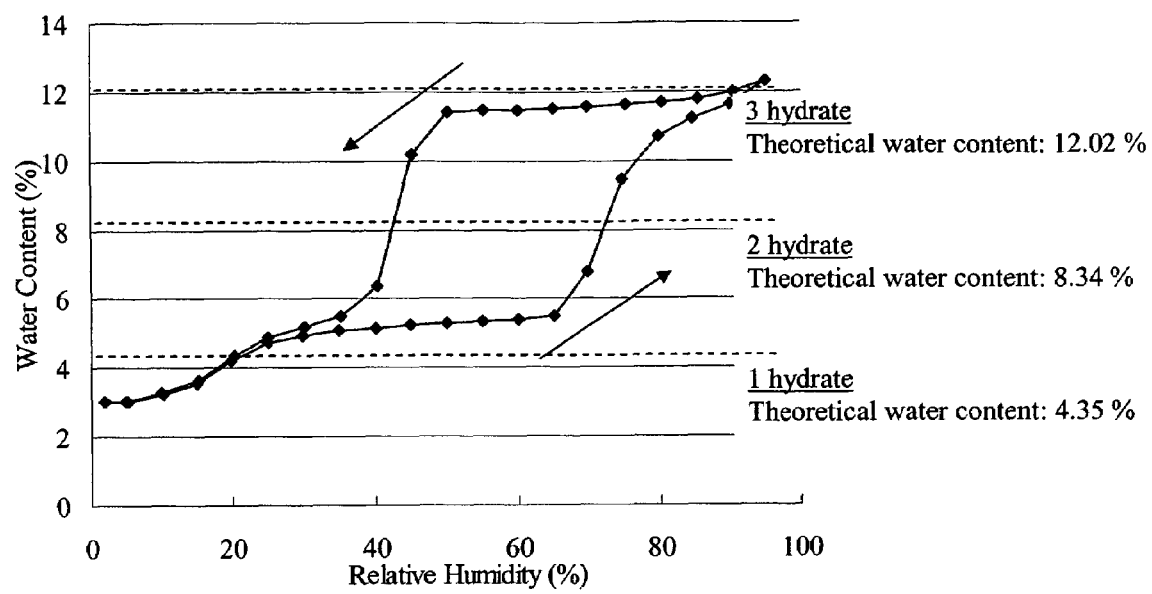
FIG. 2 shows moisture adsorption/desorption isotherm at 25° C. of Cefdinir monohydrate.
Figure 3:
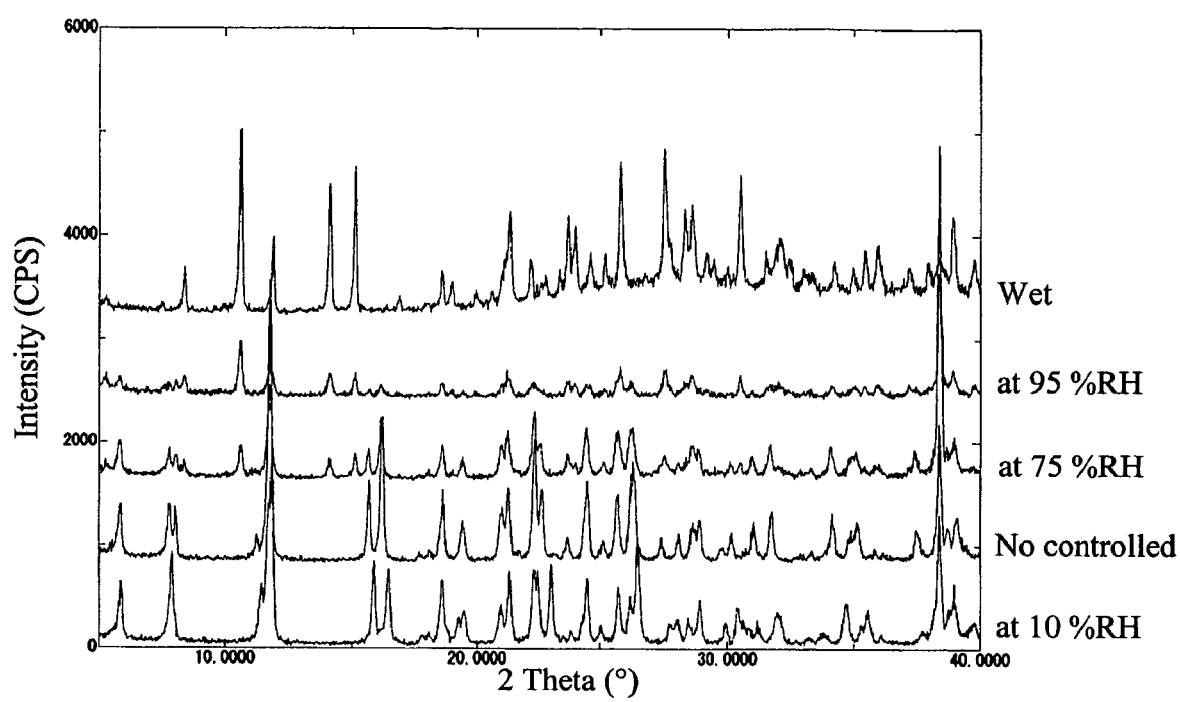
FIG. 3 shows powder X-ray diffraction pattern of Cefdinir monohydrate at various relative humidities.

The moisture adsorption/desorption isotherms of the monohydrate were measured in relative humidities of 5 to 95% at 25° C. by microbalance method (VTI MB-300W (Microbalance) and MKA-510 (Kyoto electronics MFG, LTD.)). The obtained moisture adsorption/desorption isotherm is shown in FIG. 2. The water increased to the content corresponding to higher hydrate form at the relative humidity of more than 70%, and to trihydrate at the higher relative humidity such as 95%. To confirm the crystal form at each relative humidity, the powder X-ray diffraction (PXRD) patterns were measured at the each controlled relative humidity (10, 75, and 95% RH) (Rigaku RINT TTR2 and Rigaku HUMIDITY GENERATOR HUM-1). The obtained PXRD patterns are shown in FIG. 3. It was confirm that the obtained PXRD patterns were different from that of intact sample, that is, the PXRD pattern of the monohydrate measure at no controlled relative humidity. From these results, it was considered that the monohydrate transformed to another higher hydrate (crystal form C) at high relative humidity, and crystal form C keeps 1.5 or more molecules of crystalline waters.

2-2. Solvent Medium Transformation

Figure 4:
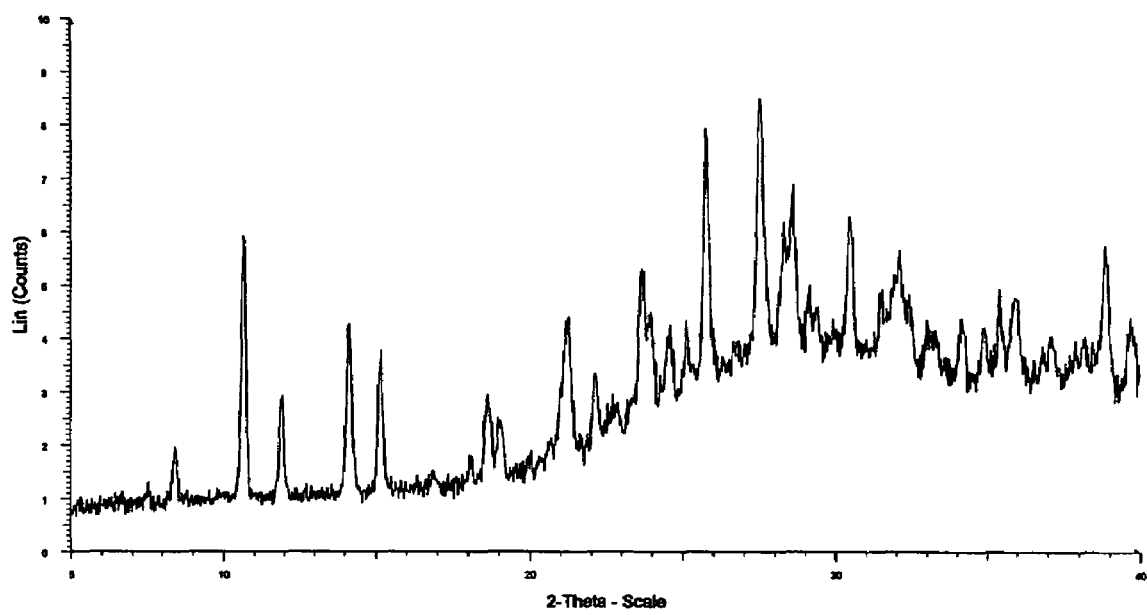
FIG. 4 shows powder X-ray diffraction pattern of Cefdinir monohydrate after stirring in water for 5 minutes.

Form A and the monohydrate were suspended in water or ethanol (99.5) at room temperature, and the powder X-ray diffraction (PXRD) patterns of the residual solid materials were measured (Bruker AXS D8 Discover with GADDS). FIG. 4 shows PXRD pattern of the residual solid obtained from the monohydrate after 5 minutes stirring in an aqueous suspension, and it was confirmed that the obtained pattern corresponded to that of another hydrate keeping much amount of molecules of crystalline water. Therefore, it was concluded that the crystalline change from monohydrate to crystal form C was occurred in an aqueous suspension.

On the other hand, form A showed no crystalline conversion to other crystal form in aqueous and ethanol suspensions.

3. Dispersibility Comparison Assay

The dispersibility of two crystal forms of Cefdinir was compared by evaluating sedimentation rates of two crystal forms. The evaluating sedimentation rate was conducted by using two methods as follow.

3-1. Method 1

Figure 5:
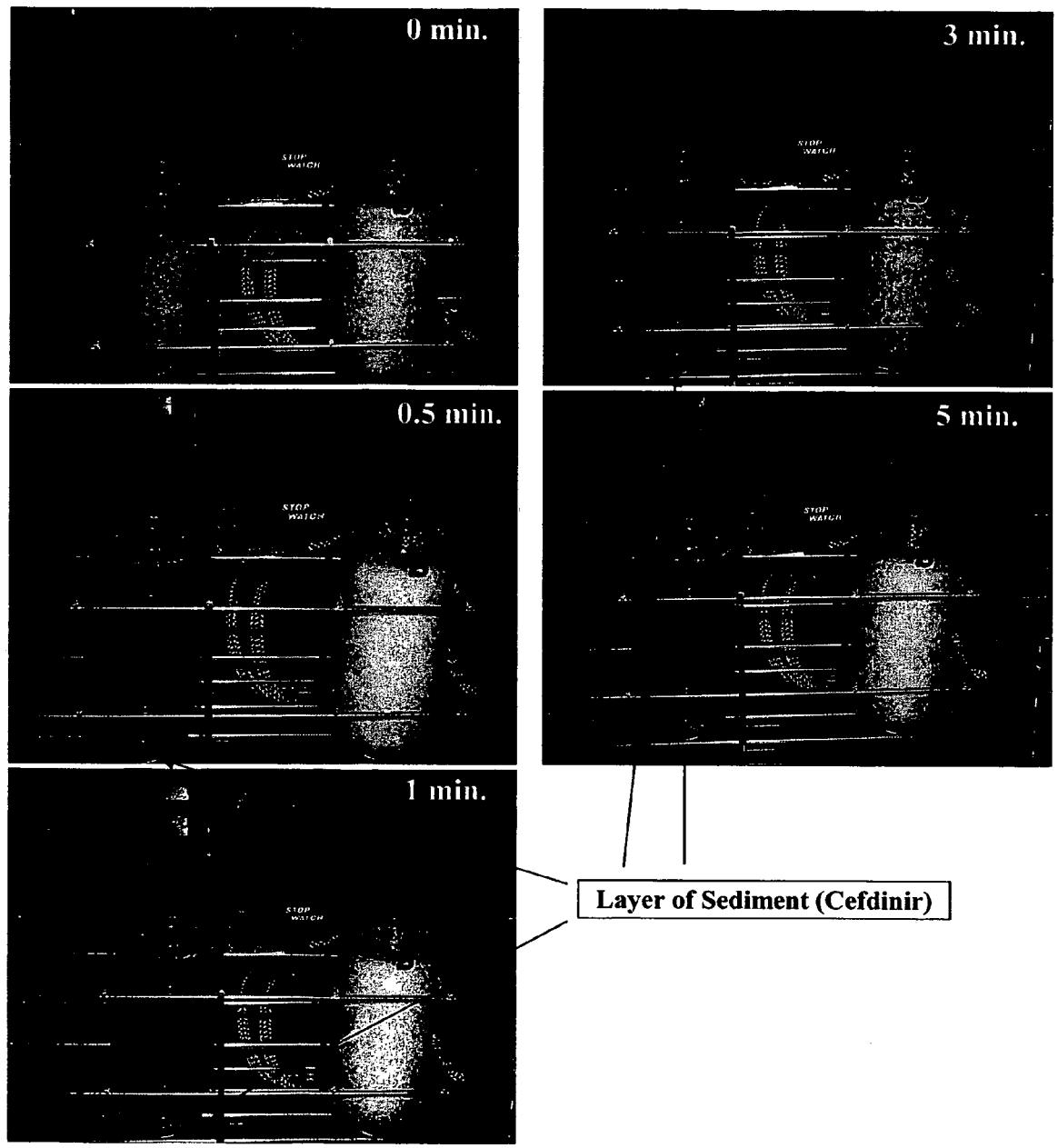
FIG. 5 shows dispersion state of crystal form A of Cefdinir and Cefdinir monohydrate.

About 1250 mg of crystal form A or the monohydrate were dispersed in 50 mL of water (125 mg/5 mL), and the suspensions were vigorously shaken by hand. Then, the appearances of contents were observed in a test tube (about sediments and lumps). The pictures of suspension states were taken with time. As shown in FIG. 5, the dispersion state of the suspension of the monohydrate was better than that of form A, and the sedimentation rate of the monohydrate was slower than that of form A.

3-2. Method 2

Figure 6:
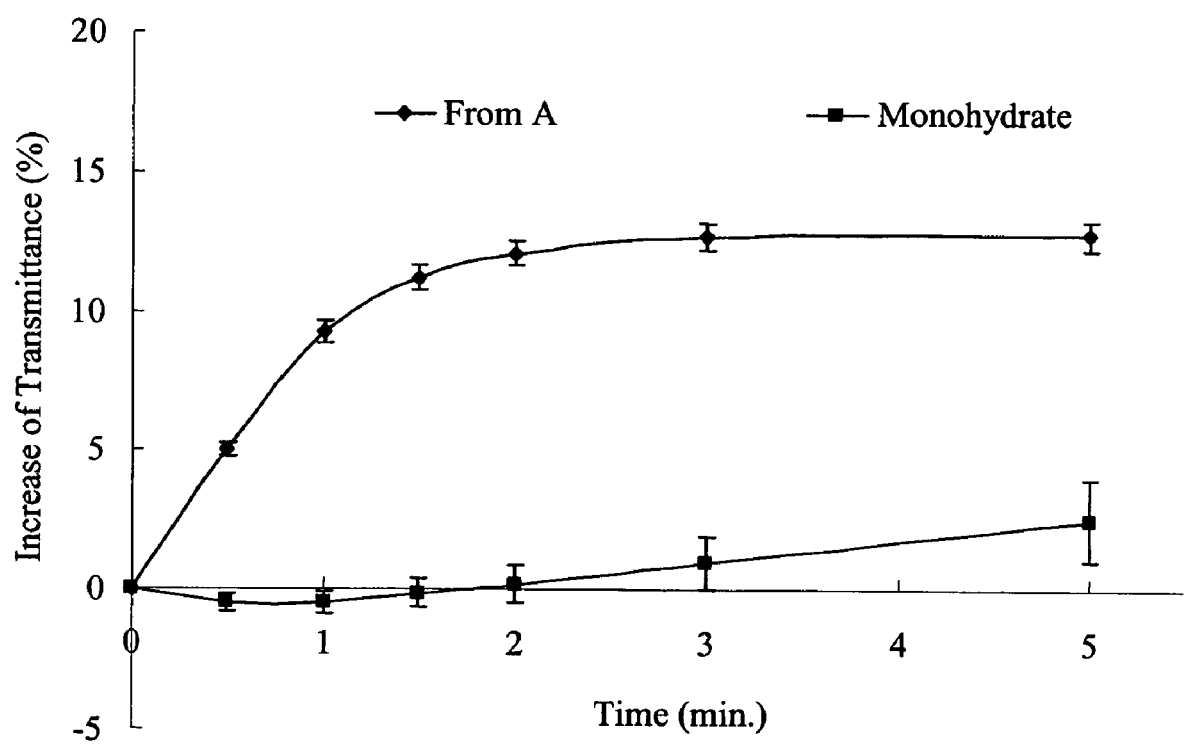
FIG. 6 shows change of transmittance of suspensions prepared with crystal form A of Cefdinir and Cefdinir monohydrate.

5 mg of crystal form A or the monohydrate were dispersed in 10 mL of water (sample concentration: 0.5 mg/mL), and the suspensions were vigorously shaken. Then, the dispersed suspensions were transferred in the cell for UV measurement, and changes of the transmittances at 650 nm were measured. As shown in FIG. 6, the transmittance of suspension prepared with form A showed the faster increase than that of the monohydrate, indicating that form A sank down faster than the monohydrate in the suspension. This result was corresponding to the observation result of dispersion rate.

The suspension properties of form A can be improved by grinding, however, this adds an additional step which is not necessary with the lower hydrates, such as the monohydrate.

The invention claimed is:

1. An oral pharmaceutical suspension comprising crystal form C of Cefdinir, and a pharmaceutically acceptable aqueous carrier.

2. The oral pharmaceutical suspension of claim 1, wherein said suspension also comprises at least one pharmaceutically acceptable additive.

3. A pharmaceutical composition comprising crystal form C of Cefdinir.

4. The oral pharmaceutical suspension of claim 1, wherein said crystal form C in the oral suspension is a higher hydrate form selected from the group consisting of sesquihydrate, dihydrate, trihydrate, trihemihydrate and tetrahydrate, or mixtures thereof.

5. The oral pharmaceutical suspension of claim 1, wherein said crystal form C in the oral suspension is Cefdinir sesquihydrate.

6. The oral pharmaceutical suspension of claim 1, wherein said crystal form C in the oral suspension is Cefdinir dihydrate.

7. The oral pharmaceutical suspension of claim 1, wherein said crystal form C in the oral suspension is Cefdinir trihydrate.

8. The oral pharmaceutical suspension of claim 1, wherein said crystal form C in the oral suspension is Cefdinir trihemihydrate.

9. The oral pharmaceutical suspension of claim 1, wherein said crystal form C in the oral suspension is Cefdinir tetrahydrate.

10. The oral pharmaceutical suspension of claim 1, wherein said pharmaceutically acceptable aqueous carrier is water.

11. The oral pharmaceutical suspension of claim 1, wherein said crystal form C of Cefdinir is in a single dose amount ranging from 10 to 1,000 mg.

12. The oral pharmaceutical suspension of claim 1, wherein said crystal form C of Cefdinir is in a single dose amount ranging from 50 to 500 mg.

13. The oral pharmaceutical suspension of claim 1, wherein said crystal form C of Cefdinir is in a single dose amount ranging from 100 to 250 mg.

14. The oral pharmaceutical suspension of claim 2, wherein said crystal form C in the oral suspension is a higher hydrate form selected from the group consisting of sesquihydrate, dihydrate, trihydrate, trihemihydrate and tetrahydrate, or mixtures thereof.

15. The oral pharmaceutical suspension of claim 2, wherein said crystal form C in the oral suspension is Cefdinir sesquihydrate.

16. The oral pharmaceutical suspension of claim 2, wherein said crystal form C in the oral suspension is Cefdinir dihydrate.

17. The oral pharmaceutical suspension of claim 2, wherein said crystal form C in the oral suspension is Cefdinir trihydrate.

18. The oral pharmaceutical suspension of claim 2, wherein said crystal form C in the oral suspension is Cefdinir trihemihydrate.

19. The oral pharmaceutical suspension of claim 2, wherein said crystal form C in the oral suspension is Cefdinir tetrahydrate.

20. The oral pharmaceutical suspension of claim 2, wherein said pharmaceutically acceptable aqueous carrier is water.

21. The oral pharmaceutical suspension of claim 2, wherein said crystal form C of Cefdinir is in a single dose amount ranging from 10 to 1,000 mg.

22. The oral pharmaceutical suspension of claim 2, wherein said crystal form C of Cefdinir is in a single dose amount ranging from 50 to 500 mg.

23. The oral pharmaceutical suspension of claim 2, wherein said crystal form C of Cefdinir is in a single dose amount ranging from 100 to 250 mg.

24. The oral pharmaceutical suspension of claim 2, wherein said pharmaceutically acceptable additive is selected from the group consisting of an auxiliary substance, a stabilizing agent, a suspending agent, a surface tension modifier, a viscosity modifier, a colorant, a preservative, a flavoring agent, lactose, citric acid, tartaric acid, stearic acid, magnesium stearate, and sucrose.

* * * * *